US 12,098,351 B2

(12) United States Patent
Damacherla et al.

(10) Patent No.: US 12,098,351 B2
(45) Date of Patent: Sep. 24, 2024

(54) DEVICE AND PROCESS FOR CONVERTING ORGANIC WASTE TO BIOGAS

(71) Applicant: Indian Oil Corporation Limited, Mumbai (IN)

(72) Inventors: Mohan Rao Damacherla, Haryana (IN); Rajesh Badhe, Haryana (IN); Manoj Kumar, Haryana (IN); Umish Srivastava, Haryana (IN); Alok Sharma, Haryana (IN); Gurpreet Singh Kapur, Haryana (IN); Sankara Sri Venkata Ramakumar, Haryana (IN)

(73) Assignee: Indian Oil Corporation Limited, Mumbai (IN)

( * ) Notice: Subject to any disclaimer, the term of this patent is extended or adjusted under 35 U.S.C. 154(b) by 565 days.

(21) Appl. No.: 17/240,163

(22) Filed: Apr. 26, 2021

(65) Prior Publication Data

US 2021/0332313 A1    Oct. 28, 2021

(30) Foreign Application Priority Data

Apr. 24, 2020 (IN) ............................. 202021017698

(51) Int. Cl.
*C12M 1/107* (2006.01)
*C12M 1/00* (2006.01)
(Continued)

(52) U.S. Cl.
CPC ............ *C12M 21/04* (2013.01); *C12M 23/58* (2013.01); *C12M 27/02* (2013.01); *C12M 27/20* (2013.01);
(Continued)

(58) Field of Classification Search
CPC ........ C12P 5/023; C12M 21/04; C12M 21/16; C12M 23/02; C12M 23/36; C12M 33/14;
(Continued)

(56) References Cited

U.S. PATENT DOCUMENTS

| 4,022,665 A | 5/1977 | Ghosh et al. |
| 4,318,993 A | 3/1982 | Ghosh et al. |

(Continued)

FOREIGN PATENT DOCUMENTS

| CN | 2009/71358 Y | 11/2007 |
| EP | 0134766 A1 | 3/1985 |

(Continued)

OTHER PUBLICATIONS

Machine Translation of JP 2005218898 A. (Year: 2023).*
European Search Report for EP21170324.4, dated Sep. 23, 2021, 43 pgs.

*Primary Examiner* — Michael L Hobbs
(74) *Attorney, Agent, or Firm* — Blank Rome LLP

(57) ABSTRACT

The invention relates to a device and process for converting organic waste to biogas with high methane content and improved organic conversion efficiency. Disclosed process consists of two stages and in the first stage, shredded organic waste is digested in primary digester in which biodegradable organic fractions present in waste gets converted to volatile fatty acids and alcohols dissolved in aqueous solution by hydrolytic and acidogenic microorganisms. Primary digester effluent pH, is adjusted to about 6.8-7.5 by addition of controlled alkali solution. Neutralized waste slurry is separated into liquid solution called as leachate and digested solid sludge. In the second stage, liquid leachate comprising volatile fatty acids are converted to biogas with methane content in the range 80-86% by methanogenic microbial culture in main digester under anaerobic conditions. This invention further describes optimized primary and main (Continued)

digester configurations with operating conditions to improve organic conversion efficiency in both the digesters.

16 Claims, 3 Drawing Sheets

(51) Int. Cl.
    *C12M 1/06*     (2006.01)
    *C12M 1/34*     (2006.01)
    *C12R 1/01*     (2006.01)

(52) U.S. Cl.
    CPC ............ *C12M 29/00* (2013.01); *C12M 41/12* (2013.01); *C12R 2001/01* (2021.05)

(58) Field of Classification Search
    CPC ...... C12M 33/16; C12M 23/58; C12M 27/02; C12M 27/20; C12M 29/00; C12M 41/12; C12M 41/26; C12R 2001/01; C02F 11/127; C02F 11/04; C02F 11/125; C02F 2209/02; C02F 2209/06; C02F 2209/40; Y02E 50/30

See application file for complete search history.

(56) References Cited

U.S. PATENT DOCUMENTS

| | | | |
|---|---|---|---|
| 4,696,746 | A | 9/1987 | Ghosh et al. |
| 5,630,942 | A | 5/1997 | Steiner |
| 6,921,485 | B2 | 7/2005 | Kilian et al. |
| 2013/0260433 | A1 | 10/2013 | Zhang |

FOREIGN PATENT DOCUMENTS

| | | | | |
|---|---|---|---|---|
| JP | 2001/300486 A | | 10/2001 | |
| JP | 2005/218897 A | | 8/2005 | |
| JP | 2005218898 A | * | 8/2005 | ............... B09B 3/00 |
| WO | WO-2013/144703 A1 | | 10/2013 | |

* cited by examiner

DEVICE AND PROCESS FOR CONVERTING ORGANIC WASTE TO BIOGAS

RELATED APPLICATION

This application claims the benefit of Indian Application No. 202021017698, filed on Apr. 24, 2020. The entire disclosure of this application is hereby incorporated by reference.

FIELD OF THE INVENTION

The present invention relates to a device and process for converting organic waste to biogas with high methane content and improved organic conversion efficiency. More particularly, this invention relates to primary and main digester configurations to improve organic conversion efficiency and generate biogas with high methane content in a two stage biomethanation process. In the primary digester, hydrolysis and acidification of organic waste in the presence of mixed microbial consortium generates volatile fatty acids and alcohols dissolved in aqueous phase. Liquid solution comprising volatile fatty acids are converted to biogas in the main digester by methanogenic microbial culture under anaerobic conditions.

BACKGROUND OF THE INVENTION

Biomethanation is a process in which organic waste is microbiologically decomposed under anaerobic conditions to biogas. Biogas is a mixture of mainly methane, carbon dioxide, and small quantities of nitrogen and hydrogen sulfide. Biogas can be used for various applications such as cooking, heating, power generation; and as a transportation fuel after up-grading to bio-CNG/bio-methane. Biomethanation process also generates stabilized solid residue which can be used as bio-fertilizer. Various organic carbonaceous resources that can be treated in biomethanation are food waste, municipal solid waste, sewage sludge, biomass, crop residue etc. Operating parameters such as organic waste composition, loading rate, pH, temperature, and retention time affect the performance of biomethanation process.

Conversion of complex organic matter to methane and carbon dioxide is performed by combined action of four different groups of microorganisms. The essential microbial complex is comprised of hydrolytic enzymes, acidogenic bacteria, acetogenic bacteria and methanogenic archaea. Hydrolytic enzymes decompose complex organic molecules (carbohydrates, lipids, proteins etc.) to soluble monomers (sugars, long-chain fatty acids, glycerol, amino acids, etc.). Acidogenic bacteria converts these soluble monomers to short chain fatty acids (butyrate, propionate, acetate, etc.), alcohols (ethanol and methanol), hydrogen, and carbon dioxide. Short chain fatty acids and alcohols are converted to hydrogen, acetate, formate, and carbon dioxide by acetogenic bacteria. These end products are finally converted to methane and carbon dioxide by methanogenic archaea.

Treatment of organic waste using biomethanation process poses several challenges due to non-uniformity of feedstock. Organic fraction of municipal solid waste (MSW) contains agricultural leafy biomass, food waste and paper in varying concentrations. Further, MSW is usually contaminated with non-biodegradable fractions such as glass, plastics, and metals. Hence, segregation of feedstock is essential to separate these non-biodegradable materials before processing in biomethanation plant.

Composition of raw biogas generated from biomethanation process is typically 55-65 percent methane, 35-45 percent carbon dioxide and less than 1 percent hydrogen sulfide. This biogas is required to undergo expensive additional gas cleaning and upgradation to generate biogas meeting piped natural gas and automotive compressed natural gas (CNG) requirements. Downstream gas upgradation processing cost can be reduced by improving methane percentage in the generated biogas.

Most of the conventional biomethanation technologies for treating organic waste are single stage and can handle total solids (TS) up to 10%. Total solids concentration of the waste influences the pH and effectiveness of the microorganisms in decomposition of organic waste. Application of high total solids in single stage digester leads to proliferation of acidogenic bacteria, and the resulting high volatile fatty acid yield triggers generation of abundant acetogenic bacteria. But metabolic efficiency of methanogenic culture decreases drastically due to decreased pH in the system. As a consequence, methanogens and acetogenic bacteria could not perform necessary reactions efficiently, which leads to metabolic imbalance and process deterioration.

Two stage biomethanation process addresses the inhibitory effects of high volatile fatty, acid concentration on methanogenic bacteria by performing acidification and methanogenesis in two different digesters. In the primary digester, microbial population and operating conditions are selected to promote conversion of organic carbonaceous waste to lower molecular weight volatile fatty acids and alcohols. The soluble volatile fatty acids in the aqueous phase, called as liquid leachate, gets separated from digested sludge and transferred to main digester. In the main digester, methanogenic microorganisms convert volatile fatty acids to biogas. Two stage digestion process increases methane content of biogas to about 70 percent and provide better control of operating conditions in both the stages. Further, acidification reactor of two stage process accepts organic waste with high total solids content.

Several reported literatures describe two stage biomethanation process with the objective of enhancing organic conversion efficiency and improving methane content in biogas. U.S. Pat. Nos. 4,022,665 and 4,318,993 describes a two-stage anaerobic digestion process in which organic waste is efficiently breakdowns down to lower molecular weight acids in the first stage with retention times of less than two days. Lower molecular weight acids along with digested sludge are converted to biogas in second stage with retention times of about two to seven days. It also describes organic loading rate and pH in both stages and further treatment of effluent from methanogenic reactor in another methanogenic reactor.

U.S. Pat. No. 4,696,746 also teaches two stage biomethanation process as described in U.S. Pat. Nos. 4,022,665 and 4,318,993. But, in this patent liquid effluent from $1^{st}$ stage i.e. acidification phase is first passed to methane forming digester and gaseous product from first stage is passed to second separate methane forming digester for production of methane in first and second methane forming digesters. It also claims that two separate methane forming digesters provide increased overall methane production.

U.S. Pat. No. 6,921,485 describes two stage biomethanation process in which organic waste is digested in acidification reactor to produce volatile acids dissolved in water and suspended solids forming sludge effluent. The volatile acids dissolved in water are separated from solid sludge in acid separation device and volatile acids are fed to methane reactor to generate biogas. Acid and methane reactor are maintained under conditions in which formation of volatile acids and methane respectively are favored.

US patent No 2013/0260433 describes high-rate anaerobic digestion in which digestion of organic waste is carried out in three different reactors. The system comprises hydrolysis reactor for acidification of organic waste, bio-gasification reactor for converting effluent from hydrolysis reactor to biogas and bio-stabilization reactor to stabilize bio-gasification reactor effluent and increase overall energy conversion efficiency.

As per these patents, acidification of organic waste is carried out in first reactor followed by methanation of partially digested organic waste in second reactor. Few patents describe separation of first stage reactor effluent to solid and liquid fractions and adjusting chemical properties of liquid fractions before feeding into main digester. Patents disclosed in the prior art claim maximum methane content in biogas up to 70%.

The process for two stage biomethanation presented in the prior art describes increasing methane content in biogas up to 70%. Further enhancement of biogas methane content is essential to improve calorific value of biogas and reduce downstream biogas upgradation cost to generate biogas meeting automotive CNG requirements. Hence, there is a need to intensify, process and optimize reactor configurations in two stage biomethanation process for improving biogas methane content and enhancing organic conversion efficiency.

Objectives of the Present Invention:

It is an object of this invention to provide a device for improved two stage biomethanation process to enhance organic conversion efficiency and generate biogas with high methane content.

It is another object of the invention is to provide primary digester configuration for hydrolysis and acidogenesis of organic waste to convert biodegradable organic fractions into water soluble volatile fatty acids and alcohols with improved organic conversion efficiency.

It is further objective of the present invention is to provide main digester configuration for efficiently converting volatile fatty acids and alcohols to biogas with high methane content.

It is yet another object of present invention is to convert volatile fatty acids and alcohols to biogas with methane content of 80 to 86 percentages by synergistically combining improved reactor design with methanogenic bacterial inoculums.

It is yet another object of the present invention is to provide process conditions in both primary and main digesters to enhance organic conversion efficiency and generate biogas with high methane content.

Summary of Title Invention:

This summary is provided to introduce a selection of concepts, in a simplified format, that are further described in the detailed description of the invention. This summary is neither intended to identify key or essential inventive concepts of the invention and nor is it intended to determine the scope of the invention.

In one of the embodiments, the invention discloses a device and process for enhancing biogas methane content with improved organic conversion efficiency in a two stage biomethanation process. Biogas methane content is improved by optimizing main digester configuration, operating conditions and deploying high performing microbial culture. Organic conversion efficiency in both primary and main digesters is enhanced through improved reactor configurations with optimized operating conditions.

In yet one of the embodiments, the present invention provides a process for carrying out anaerobic digestion of organic waste to biogas. The said process comprising of two stages. In the first stage, organic waste slurry comprising 10 to 15 percentage total solids concentration undergoes hydrolysis and acidification by hydrolytic and acidogenic microorganisms under anaerobic conditions. Products of the first stage are biogas, volatile fatty acids and alcohols dissolved in aqueous phase(leachate) and digested solid sludge. pH of the first stage effluent is adjusted to about 6.8-7.5 by adding alkali solution. Then the neutralized liquid leachate gets separated from digested solid sludge using solid liquid separator. During second stage, volatile fatty acids present in leachate are converted to biogas by methanogenic microbial culture under anaerobic conditions.

In yet another embodiment, the present invention provides a device comprising of i) feed preparation tank in which required quantity of water is added to the shredded organic waste and thoroughly mixed to prepare homogenized feed mixture ii) first slurry pump to feed organic waste slurry from feed tank to primary digester iii) primary digester in which hydrolytic and acidogenic microorganism digests organic waste and generates biogas, volatile fatty acids and alcohols, and digested solid sludge iv) neutralization tank in which pH of the primary digester effluent is adjusted to 6.8-7.5 by adding alkali solution v) second slurry pump to feed neutralized primary digester effluent to solid liquid separator vi) solid liquid separator to separate digested organic waste to solid sludge and liquid leachate vii) feed holding rank to hold neutralized liquid leachate comprising volatile fatty acids and alcohols viii) feed pump to feed neutralized liquid leachate to main digester ix) main digester to convert neutralized liquid leachate to biogas by methanogenic microbial culture x) tube settler to separate residual suspended solid particles present in main digester liquid effluent xi) gas balloon to store generated biogas.

In yet another embodiment, the present invention provides a primary digester (17) of a device (1) for converting homogenized organic waste slurry (15) to biogas (18) and digested organic waste slurry (19) comprising;
- a cylindrical body or rectangular body reactor;
- one inlet opening (40) to receive organic waste slurry (15);
- two outlet openings (47, 48) for digested waste slurry (19) and generated biogas (18);
- plurality of internal baffle plates (41) adapted to guide organic waste slurry (15) flow direction, avoid short circuit and back mixing of primary digester (17) contents;
- the internal baffles divide the primary digester (17) into plurality of chambers;
- each chamber comprises of;
- a horizontal or a vertical agitator (42) for mixing the primary digester (7) contents;
- a temperature sensor (43);
- a heater (44);
- a temperature controller (45);
- a thermal insulation (49) to avoid heat loss and maintain temperature in the range of 35-45 deg C;
- a drain valve (46) in each chamber adapted to separate non-biodegradable fractions settled at the bottom of the primary digester (17), wherein organic waste slurry (15) in each chamber has a hydraulic residence time of 36-60 hours.

In yet another embodiment, the present invention provides a main digester (29) of a device (1) for converting volatile fatty acids present in neutralized leachate (25) to biogas (30) with high methane content comprising;
 a cylindrical body or rectangular body reactor;
 one inlet opening (51) to receive neutralized leachate (25);
 two outlet openings (59,58) for digested effluent (31) and generated biogas (30);
 pebbles (53) or any other packing medium for retaining and promote growth of microbial inoculumsplurality of internal baffle plates (52) adapted to guide neutralized leachate (25) flow direction, avoid short circuit and back mixing of main digester (29) contents; the internal baffles divide main digester (29) into a minimum two of chambers;
 each chamber comprises of;
 a temperature sensor (54);
 a heater (55);
 a temperature controller (56)
 a thermal insulation (60) to avoid heat loss and maintain temperature in the range of 35-45 deg C;
 a drain valve (57) in each chamber (A1, B1) adapted to drain out settled non-biodegradable fractions from digester bottom; wherein the hydraulic residence time in each chamber is 24-48 h depending on COD of leachate.

In yet another embodiment, the present invention provides a device (1) for converting organic waste (10) to biogas (18, 30) comprising;
 a shredder (11) adapted to shred organic waste (10) to shredded organic waste (12) reduced in particle size;
 a feed preparation tank (14) adapted to hold the shredded organic waste (12) and water (13) to prepare a homogenized organic waste slurry (15);
 a first slurry pump (16) adapted to transfer organic waste slurry (15) from the feed preparation tank (14) to a primary digester (17), wherein the primary digester (17) is adapted to convert the biodegradable organic fractions in the organic waste slurry (15) to biogas (18) and digested organic waste slurry (19) comprises of water soluble volatile fatty acids and alcohols;
 a neutralization tank (20) adapted to change the pH of the digested organic waste slurry (19) by adding alkali solution (21);
 a second slurry pump (23) adapted to feed neutralized primary digested slurry (22) to a solid liquid separator (24);
 the solid liquid separator (24) adapted to separate neutralized primary digested slurry (22) to a solid sludge (26) and a liquid leachate (25);
 a feed holding tank (27) adapted to hold the liquid leachate (25) comprising volatile fatty acids and alcohols;
 a feed pump (28) to feed the liquid leachate (25) to a main digester (29), wherein the main digester (29) is adapted to convert the liquid leachate (25) to biogas (30) by methanogenic microbial culture;
 a tube settler (34) adapted to separate the residual solid sludge (35) from the main digester (29) overflow effluent (31) and generate liquid stream (36) for further usage; and
 a biogas balloon (32) adapted to store generated biogas (30);
 wherein the primary digester (17) of the device (1) for converting homogenized organic waste slurry (15) to biogas (18) and digested organic waste slurry (19) comprising;
 a cylindrical body or rectangular body reactor;
 a one inlet opening (40) to receive organic waste slurry (15);
 a two outlet openings (47, 48) for digested waste slurry (19) and generated biogas (18);
 plurality of internal baffle plates (41) adapted to guide organic waste slurry (15) flow direction, avoid short circuit and back mixing of primary digester (17) contents;
 wherein the internal baffles (41) divide the primary digester (17) into a minimum of three chambers;
 each chamber comprises of;
 a horizontal or a vertical agitator (42) for mixing the primary digester (17) contents;
 a temperature sensor (43);
 a heater (44);
 a temperature controller (45)
 a thermal insulation (49) to avoid heat loss and maintain temperature in the range 35-45 deg C;
 a drain valve (46) in each chamber adapted to separate non-biodegradable fractions settled at the bottom of the primary digester (17).

In yet another embodiment the present invention provides a device (1) for converting organic waste (10) to biogas (18, 30) comprises of a primary digester wherein the organic waste slurry (15) in each chamber created by a plurality of internal baffle plates (41) adapted to guide organic waste slurry (15) flow direction, avoid short circuit and back mixing of primary digester (17) contents has a residence time of 36-60 hours.

In yet another embodiment, the present invention provides a device (1) for converting organic waste (10) to biogas (18, 30) comprising;
 a shredder (11) adapted to shred organic waste (10) to shredded organic waste (12) reduced in particle size;
 a feed preparation tank (14) adapted to hold the shredded organic waste (12) and water (13) to prepare a homogenized organic waste slurry (15);
 a first slurry pump (16) adapted to transfer organic waste slurry (15) from the feed preparation tank (14) to a primary digester (17), wherein the primary digester (17) is adapted to convert the biodegradable organic fractions in the organic waste slurry (15) to biogas (18) and digested organic waste slurry (19) comprises of water soluble volatile fatty acids and alcohols;
 a neutralization tank (20) adapted to change the pH of the digested waste slurry (19) by adding alkali solution (21);
 a second slurry pump (23) adapted to feed neutralized primary digested slurry (22) to a solid liquid separator (24);
 the solid liquid separator (24) adapted to separate neutralized primary digested slurry (22) to a solid sludge (26) and a liquid leachate (25);
 a feed holding tank (27) adapted to hold the liquid leachate (25) comprising volatile fatty acids and alcohols;
 a feed pump (28) to feed the liquid leachate (25) to a main digester (29), wherein the main digester (29) is adapted to convert the liquid leachate (25) to biogas (30) by methanogenic microbial culture;
 a tube settler (34) adapted to separate the residual solid sludge (35) from main digester (29) overflow effluent (31) and generate liquid stream (36) for further usage; and
 a biogas balloon (32) adapted to store generated biogas (30);
 wherein the main digester (29) of a device (1) for converting volatile fatty acids present in neutralized leachate (25) to biogas (30) with high methane content comprising;
 a cylindrical body or rectangular body reactor;

one inlet opening (51) to receive neutralized leachate (25);

two outlet openings (59,58) for digested effluent (31) and generated biogas (30);

pebbles (53) or any other packing medium for retaining and promote growth of microbial inoculums a plurality of baffle plates (52) adapted to guide neutralized leachate (25) flow direction, avoid short circuit and back mixing of main digester (29) contents;

the internal baffles divide main digester (29) into a minimum of two chambers;

each chamber comprises of;

a temperature sensor (54);

a heater (55);

a temperature controller (56)

a thermal insulation (60) to avoid heat loss and maintain temperature in the range of 35-45 deg C;

a drain valve (57) in each chamber (A1, B1) adapted to drain out settled non-biodegradable fractions from digester bottom.

In yet another embodiment of the present invention provides a device (1) for converting organic waste (10) to biogas (18, 30) comprises of a main digester, wherein the neutralized leachate (25) in each chamber created by a plurality of internal baffle plates (52) has a hydraulic residence time of 24-48 hours depending on COD of the leachate.

In yet another embodiment of the present invention provides a device (1) for converting organic waste (10) to biogas (18, 30) comprises of a primary digester and a main digester, wherein chambers created in primary (17) and main digester (29) by a plurality of internal baffle plates (41, 52) has a residence time of residence time of 36-60 hours and 24-48 hours respectively.

In yet another embodiment, the present invention provides a hydrolysis and acidification of organic carbonaceous feedstock comprising 10-15% total solids is carried out by mixed microbial culture in primary digester. Digester configuration was optimized to process high total solids with maximum organic conversion efficiency. Mixed microbial culture present in primary digester converts biodegradable organic fractions to principally volatile fatty acids such as acetic acid, propionic acid, butyric acid, etc. and alcohols. Mixed microbial culture, which are well known in the prior art, is used for hydrolysis and acidification of organic waste. Biogas generated in the primary digester principally consists of carbon dioxide, hydrogen and small quantities of methane. pH of primary digester effluent is in the range 4.5 to 6.0. Digested effluent pH is adjusted to about 6.8-7.5 by adding controlled amount of alkali solution. Neutralized digested slurry is separated into liquid leachate comprising volatile fatty acids and alcohols and digested solid sludge using solid liquid separator.

In yet another embodiment, the present invention provides a neutralized leachate that is admitted to main digester in which methanogenic microbial culture converts volatile fatty acids to biogas. Main digester configuration and operating conditions are optimized to generate biogas with 80 to 86 percentage methane and 12-17% carbon dioxide. Methanogenic microbial culture known in prior art is used in the main digester.

To further clarify the advantages and features of the present invention, a more particular description of the invention will be rendered by reference to specific embodiments thereof, which is illustrated in the appended drawings. It is appreciated that these drawings depict only typical embodiments of the invention and are therefore not to be considered limiting of its scope. The invention will be described and explained with additional specificity and detail with the accompanying drawings.

BRIEF DESCRIPTION OF THE ACCOMPANYING DRAWINGS

These and other features, aspect, and advantages of the present invention will become better understood when the following detailed description is read with reference to the accompanying drawings in which like characters represent like parts throughout the drawings, wherein the device and process and digester configurations described in the present invention are explained in more detail with reference to the following drawings.

DETAILED DESCRIPTION OF A PREFERRED EMBODIMENT OF TILE INVENTION

Figure 1:
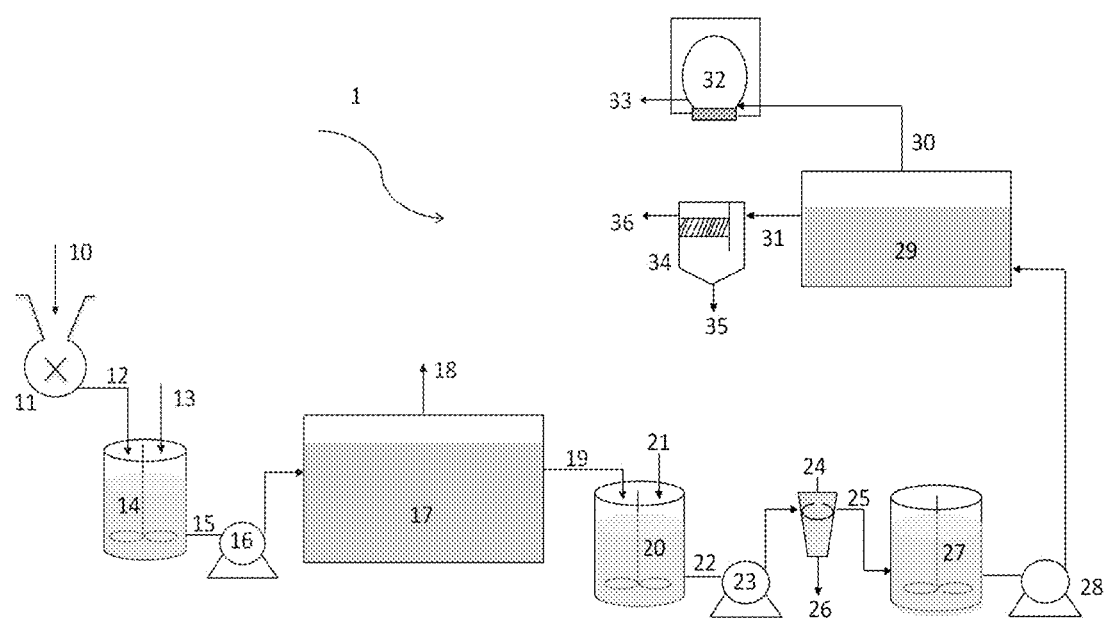
FIG. 1 illustrates a schematic block diagram of device illustrating features of preferred embodiment of this invention in connection with conversion of organic waste to biogas.

For the purpose of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated system, and such further applications of the principles of the invention as illustrated therein being contemplated as would normally occur to one skilled in the art to which the invention relates. Unless otherwise defined, all technical and scientific terms used herein have the same meaning as commonly understood by one of ordinary skilled in the art to which this invention belongs. The system, methods, and examples provided herein are illustrative only and not intended to be limiting.

The term "some" as used herein is defined as "none, or one, or more than one, or all." Accordingly, the terms "none," "one," "more than one," "more than one, but not all" or "all" would all fall under the definition of "some." The term "some embodiments" may refer to no embodiments or to one embodiment or to several embodiments or to all embodiments. Accordingly, the term "some embodiments" is defined as meaning "no embodiment, or one embodiment, or more than one embodiment, or all embodiments."

The terminology and structure employed herein is for describing, teaching and illuminating some embodiments and their specific features and elements and does not limit, restrict or reduce the spirit and scope of the claims or their equivalents.

More specifically, any terms used herein such as but not limited to "includes," "comprises," "has," "consists," and grammatical variants thereof do NOT specify an exact limitation or restriction and certainly do NOT exclude the possible addition of one or more features or elements, unless otherwise stated, and furthermore must NOT be taken to exclude the possible removal of one or more of the listed features and elements, unless otherwise stated with the limiting language "MUST comprise" or "NEEDS TO include."

Whether or not a certain feature or element was limited to being used only once, either way, it may still be referred to as "one or more features" or "one or more elements" or "at least one feature" or "at least one element." Furthermore, the use of the terms "one or more" or "at least one" feature or element do NOT preclude there being none of that feature or element, unless otherwise specified by limiting language such as "there NEEDS to be one or more . . . " or "one or more element is REQUIRED."

Unless otherwise defined, all terms, and especially any technical and/or scientific terms, used herein may be taken to have the same meaning as commonly understood by one having ordinary skills in the art.

Reference is made herein to some "embodiments," It should be understood that an embodiment is an example of a possible implementation of any features and/or elements presented in the attached claims. Some embodiments have been described for the purpose of illuminating one or more of the potential ways in which the specific features and/or elements of the attached claims fulfil the requirements of uniqueness, utility and non-obviousness.

Use of the phrases and/or terms such as but not limited to "a first embodiment," "a further embodiment," "an alternate embodiment," "one embodiment," "an embodiment," "multiple embodiments," "some embodiments," "other embodiments," "further embodiment", "furthermore embodiment", "additional embodiment" or variants thereof do NOT necessarily refer to the same embodiments. Unless otherwise specified, one or more particular features and/or elements described in connection with one or more embodiments may be found in one embodiment, or may be found in more than one embodiment, or may be found in all embodiments, or may be found in no embodiments. Although one or more features and/or elements may be described herein in the context of only a single embodiment, or alternatively in the context of more than one embodiment, or further alternatively in the context of all embodiments, the features and/or elements may instead be provided separately or in any, appropriate combination or not at all. Conversely, any features and/or elements described in the context of separate embodiments may alternatively be realized as existing together in the context of a single embodiment.

Any particular and all details set forth herein are used in the context of some embodiments and therefore should NOT be necessarily taken as limiting factors to the attached claims. The attached claims and their legal equivalents can be realized in the context of embodiments other than the ones used as illustrative examples in the description below.

Embodiments of the present invention will be described below in detail with reference to the accompanying drawings.

While the invention is susceptible to various modifications and/or alternative adaptations, specific embodiment thereof has been shown by way of examples and will be described in detail below. However, it should be understood, that it is not intended to limit the invention to the particular structural arrangement disclosed, but on the contrary, the invention is to cover all modifications, structural adaptations and alternative falling within the spirit and the scope of the invention as defined herein.

FIG. 1 illustrates an overall layout of the preferred embodiment of present invention illustrating a device (1) for biomethanation of organic waste (10) to biogas (18,30) with high methane content and improved organic conversion efficiency. The device (1) deploys a two stage biomethanation process according to an embodiment of the present disclosure for efficiently converting organic waste (10) to biogas (18,30). The biogas methane content and organic conversion efficiency are improved by optimizing device (1) digester configurations and operating conditions in both the primary and main digesters. The device (1) generates biogas with methane content in the range 80-86% and organic conversion efficiency of more than 80% in primary digester and 90% in main digester.

The device (1) may be employed to convert organic waste (10) to biogas (18, 30) and may include a shredder (11) adapted to shred organic waste (10) to shredded organic waste (12) that has a reduced particle size is in the range of 2-15 mm.

The device (1) may further include a feed preparation tank (14) that is adapted to hold the shredded organic waste (12) and water (13) to prepare homogenized organic waste slurry (15). The device (1) may also include a first slurry pump (16) adapted to transfer organic waste slurry (15) from the feed preparation tank (14) to a primary digester (17).

The primary digester (17) of the device (1) is adapted to convert the biodegradable organic fractions in the organic waste slurry (15) to biogas (18) and digested waste slurry (19). The digested waste slurry (9) comprises of water soluble volatile fatty acids and alcohols. The digestion of organic waste to digested organic waste slurry is carried out by hydrolytic and acidogenic microorganisms.

The device may further include a neutralization tank (20) adapted to change the pH of the digested waste slurry (19) by adding alkali solution (21) such as slaked lime, sodium hydroxide and sodium carbonate to form neutralized digested waste slurry (22). The pH change of the digested waste slurry (19) is in the range of 6.8-7.5.

As shown in FIG. 1, the device (1) may include a second slurry pump (23) adapted to feed the neutralized primary digested slurry (22) to a solid liquid separator (24). The solid liquid separator (24) is adapted to separate neutralized primary digested slurry (22) to a solid sludge (26) and a liquid leachate (25). The device may (1) may further include a feed holding tank (27) adapted to hold the liquid leachate (25) comprising volatile fatty acids and alcohols.

The device (1) may include a teed pump (28) to feed the liquid leachate (25) to a main digester (29), wherein the main digester (29) is adapted to convert the liquid leachate (25) to biogas (30) by methanogenic microbial culture.

The device further includes a tube settler (34) adapted to separate the residual solid sludge (35) from main digester (29) overflow effluent (31); and a biogas balloon (32) adapted to store generated biogas (30).

The process of conversion of organic waste (10) to biogas (18, 30) comprises of a two stage biomethanation. In the first stage organic waste (10) is segregated from non-biodegradable organics such as glass, metals, plastics, paper etc. The segregated organic waste (10) is shredded or grounded using a shredder (11) to reduce particle size to about 2-15 mm size. The shredded organic waste (12) is loaded into a feed preparation tank (14) in which required quantity of water (13) is added to prepare homogenized waste slurry (15) with 10-15% total solids. The homogenized waste slurry (15) from the feed preparation tank is transferred to a primary digester (17) using first slurry pump (16). In the primary digester (17), complex biodegradable organic fractions present in homogenized organic waste slurry (15) gets converted to biogas (18) and digested waste slurry (19) comprising water soluble volatile fatty acids and alcohols by hydrolytic and acidogenic microorganisms. The feedstock of homogenized organic waste slurry (15) to primary digester (17) may be introduced intermittently or continuously.

In the second stage of the two stage biomethanation of organic waste the digested waste slurry (19) from the primary digester (17) is taken to a neutralization tank (20) in which pH of the digested waste slurry (19) is adjusted to about 6.8 to 7.5 by adding slaked lime solution (21). Other alkali solutions such as sodium hydroxide, sodium carbonate may also be used for neutralization. The neutralized digested waste slurry (22) is pumped to a mechanical solid liquid separator (24) such as a screw filter press or a centrifuge using a second slurry pump (23) to separate the neutralized digested waste slurry (22) into liquid leachate (25) comprising volatile fatty acids and alcohols and digested solid sludge (26). The liquid leachate (25) leaving solid liquid separator is taken to a feed holding tank (27). The neutralized liquid leachate (25) is continuously or intermittently fed from the feed holding tank (27), to a main digester (29) by a feed pump (28). In the main digester (29) high performing bacterial inoculum converts volatile fatty acids present in the liquid leachate (25) to biogas (30) and an effluent (31). The effluent (31) overflowing from the main digester (29) is taken to a tube settler (34) to separate residual solid sludge (35) from a liquid fraction (36). The biogas (30) generated in the main digester (29) is collected in biogas balloon (32) from where it is routed to end application).

Figure 2:
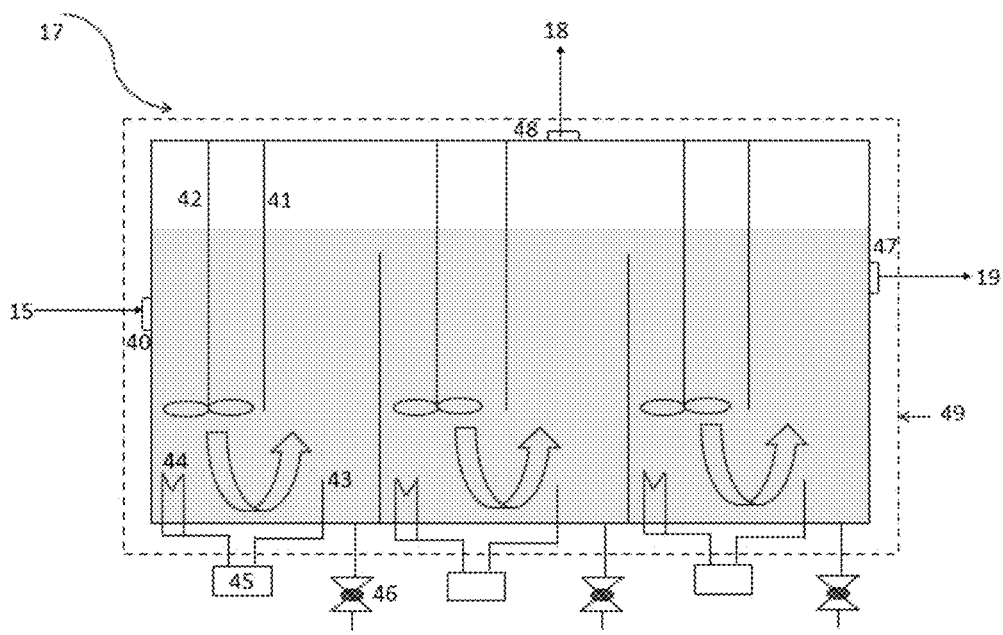
FIG. 2 illustrates a schematic of digester configuration illustrating features of another preferred embodiment of this invention in connection with primary digester.

FIG. 2 schematically illustrates a primary digester (17) configuration for digesting organic waste (10) continuously. The primary digester (17) may be designed to be horizontal, cylindrical or rectangular reactor. However, it should be appreciated by a person skilled in the art that it should not be construed as limiting, and primary digester (17) may have any other shape without departing from the scope of the present disclosure. The primary digester has one inlet opening (40) to receive organic waste slurry (15) and two outlet openings (47, 48) to discharge digested slurry (19) and generated biogas (18). The hydrolytic and acidogenic microorganisms present in primary digester (17) convert complex organic molecules to simpler volatile fatty acids, other organic intermediates and biogas. Biogas (18) generated in primary digester (17) primarily consists of carbon dioxide with minor quantities of hydrogen and methane. The pH of digested waste slurry (19) leaving the primary digester (17) is in the range 4.5 to 6.0. Primary digester (17) hydraulic retention time (HRT) is about 4 to 8 days depending on nature of feedstock and organic loading. Temperature inside the primary digester is maintained in the range 35-45 degree Centigrade using heating arrangement with temperature controller and thermal insulation.

The primary digester (17) has internal baffle plates (41) to guide organic waste slurry (15) flow direction, avoid short circuit and back mixing of reactor contents. The number of baffles may vary. However, a minimum of three downward and two upward projecting baffles plates are provided in primary digester for efficiently converting biodegradable fractions of organic waste slurry (15) to volatile fatty acids and alcohols. Internal baffles (41) divide primary digester (17) into minimum of three chambers and each chamber is provided with horizontal or vertical agitator (42) for mixing the chamber contents. The primary digester (17) is also mounted with a temperature sensor (43), a heater (44), a temperature controller (45) and a thermal insulation (49) to maintain temperature in the range 35-45 degree Centigrade at all the times. A drain valve (46) is provided in each chamber of the primary digester (17) to separate non-biodegradable fractions that are settled at the bottom of the primary digester (17). Residence time in each chamber is 36-60 h depending on organic loading rate and nature of the feed stock.

Organic waste slurry (15) being pumped to primary digester (17) transfers partially, digested slurry which has spent 36-60 hours in the first chamber to the second chamber. Partially, digested organic slurry (15) being transferred from the first chamber to second chamber, transfers same quantity of digested waste from the second chamber to third chamber. Primary digester (17) with indicated residence times reduces volatile solids (VS) contents by more than 85% and 80% for food and vegetable wastes respectively.

Figure 3:
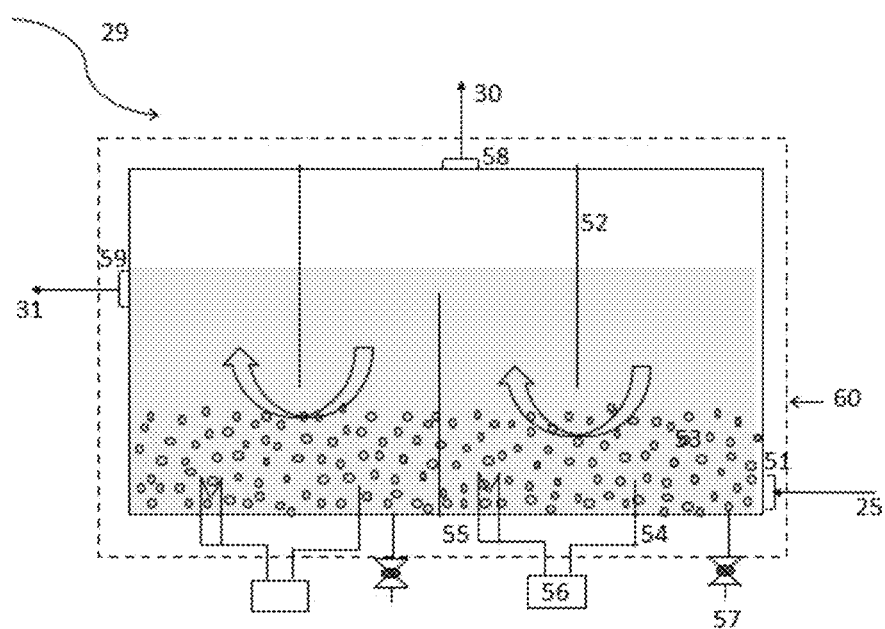
FIG. 3 illustrates a schematic of digester configuration illustrating features of another preferred embodiment of this invention in connection with main digester.

FIG. 3 schematically illustrates a main digester (29) configuration for converting volatile fatty acids present in liquid leachate (25) to biogas (30) with high methane content by methanogenic microbial culture under anaerobic conditions. The main digester (29) may be horizontal, cylindrical or rectangular packed bed reactor. However, it should be appreciated by a person skilled in the art that it should not be construed as limiting, and main digester (29) may have any other shape without departing from the scope of the present disclosure. The horizontal arrangement with internal baffles (52) of the main digester provides more surface area which assist for better mass transfer and improved conversion of organic fractions to biogas (30) with high methane content. Main digester (29) has one inlet port (51) to receive neutralized leachate (25) and two outlet ports (58.59). One of the outlet ports may be for discharging the digested effluent (31) and another for generated biogas (30). It is also provided with internal baffle plates (52) to guide leachate (25) flow direction, avoid short circuit and back mixing of reactor contents. A minimum two downward and one upward projecting baffles (52) are provided for efficient conversion of leachate (25) to biogas (30) with high methane content. The number of baffles may vary. About 20% of the main digester (29) volume is filled with pebbles (53) or any other packing medium for retaining and to promote growth of microbial inoculums. The hydraulic retention time (HRT) in main digester (29) is 2 to 4 days depending on organic loading in liquid influent. Further, main digester (29) is provided with a thermal insulation (60) to prevent heat loss. Internal temperature of main digester (29) is maintained in the range of 35-40 degree Centigrade at all times with the help of a temperature controller (56). Digested leachate overflow leaving main digester is routed to a tube settler (34) to separate residual solids (35) present in liquid effluent (31). Biogas (30) generated in main digester (29) consists of 80-86% methane, 12-17% carbon dioxide and trace quantities of nitrogen and hydrogen sulfide. Alternative digester configuration know in the prior art such as up-flow anaerobic sludge blanket (UASB) reactor can also be used for main digester in conjunction with primary digester.

The internal baffles (52) divide main digester (29) into a minimum of two chambers. Main digester (29) is mounted with a temperature sensor (54), a heater (55), a temperature controller (56) and a thermal insulation (60) to maintain temperature in the range of 35-45 degree Centigrade at all the times. A drain valve (57) is provided in each chamber of main digester (29) to drain out settled non-biodegradable fractions from the main digester (29) bottom, with heating arrangement in each chamber of main digester (29). The residence time in each chamber is 24-48 hours depending on chemical oxygen demand (COI)) of leachate. The COD of neutralized leachate is reduced by more than 90% in main digester (29) and biogas (30) with methane content in the range 80-86% is generated. Volumetric ratio of primary digester (17) to main digester (29) is 1.5-3.0 to get more than 80% volatile solids (VS) reduction in primary digester (17) and 90% COD reduction in main digester (29) and generate biogas (18, 30) with 80-86% methane content. Main digester (29) length to diameter (L/D) ratio should be in the range 1-1.8 for getting desired conversion.

EXAMPLES

To evaluate performance of the device for Biomethanation organic waste, experiments were conducted in 50 kg/d biomethanation plant using food and vegetable market wastes. Performance was evaluated in terms of biodegradable organic waste conversion efficiency, biogas yield and methane content in biogas. Food waste generated in IOCL R&D Centre canteen was used for performing experiments with food waste. Vegetable market waste collected from sabzi maedi was used for conducting experiments with vegetable waste. Segregated feedstock was shredded to a particle size in the range 0.2-1.2 cm and is transferred to feed preparation tank in which required quantity of water is added. Homogenized organic waste slurry from feed preparing tank is pumped to primary digester using pump.

Primary digester is horizontal cylindrical vessel fabricated using carbon steel with internal epoxy coating. Reactor volume is 1000 L with 750 L usable volume for hydrolysis and acidification of waste slurry. Reactor is equipped with internal baffles and mechanical mixing arrangement to guide waste slurry and proper mixing of each chamber contents. Further, digester is provided with heating arrangement to maintain temperature in the range 40-45 degree Centigrade. Homogenized waste slurry is inoculated with hydrolysis and acidogenic microbial culture in feed preparation tank and pumped to primary digester. Pre-determined hydraulic retention time (HRT) was maintained in primary digester by varying feed rate to digester. Shredded feedstock and digested effluent samples were collected and analyzed for total solids (TS) and volatile solids (VS) content.

Digested effluent leaving the primary digester is collected in neutralization tank in which pH of the waste slurry is adjusted in the range 6.8-7.5 by adding slaked lime solution. Neutralized waste slurry from neutralization tank is pumped to filter press system to separate effluent into solid and liquid fractions. Liquid leachate from filter press is taken to feed holding tank in which it is inoculated with methanogenic microbial culture and continuously pumped to main digester to convert volatile fatty acids present in leachate to biogas.

Main digester was fabricated using carbon steel with internal epoxy coating. Total main digester volume is 400 L with 320 L usable volume for methanation process. Main digester is also equipped with internal baffles and heating arrangement to guide direction of leachate and maintain temperature at around 35-45 degree Centigrade, Approximately 60 Liters of gravel was added at reactor bottom to provide required surface for retaining and growth of methanogenic microorganisms. Hydraulic retention time (EMT) in methanation reactor is in the range 2 to 2.7 days depending on leachate feed rate.

Biogas samples were collected from both primary and main digesters and analyzed using Varian 4900 gas chromatograph. Biogas generated in primary digester consists of 3-9% methane, 35-89% carbon dioxide and 5-12% hydrogen. Biogas generated in main digester consists of 80-86% methane, Volume of generated biogas was measured using Ritter wet gas meter.

Organic waste feedstock characterization results with details of experiments conducted in 50 kg/d biomethanation plant are given in Table 1, Different set of experiments were conducted to study effect of organic loading rate and total solids of waste slurry in primary digester. First set of experiments were dedicated for start-up and stabilization of both primary and main digesters for 45 days using food waste as feedstock. Feed characterization results reported for each run were average of 20 days characterization after stabilization of system. Performance of primacy and main digesters for both food waste and vegetable market waste are reported in Table 2, Effluent from the main digester comes out after pre-determined hydraulic retention time. Performance parameters of main digester were also average of 20 days analysis results.

Analysis of waste feedstock and digestate samples indicates that VS removal percentage for food and vegetable wastes in primary digester are in the range 85.1-88.4 and 80.5-83.2 respectively, Analysis of neutralized leachate and main digester effluent for food and vegetable wastes indicates that chemical oxygen demand (COD) removal percentages in main digester are in the range 95.4-97.2 and 93.3-96.3 respectively. Analysis of biogas samples shows that methane content in biogas for food and vegetable wastes are in the range 83.4-85.5 and 81.1-82.3 respectively. Analysis of generated biogas indicate that biogas yield for food and vegetable wastes are in the range 0.507-0.527 $Nm^3$/kg VS and 0.422-0.425 $Nm^3$/kg VS respectively.

TABLE 1

Characterization of feed stocks and experimental details

| Sl. No | Feed stock | Characteristics | | | Waste weight (kg) | Water quantity (kg) |
| --- | --- | --- | --- | --- | --- | --- |
| | | Moisture content (%) | Total solids (%) | Volatile solids (%) | | |
| 1 | Food waste - Run 1 | 74.6 | 23.2 | 19.4 | 50.0 | 75.0 |
| 2 | Vegetable market waste - Run 2 | 70.3 | 29.7 | 23.8 | 40.0 | 60.0 |
| 3 | Food waste - Run 3 | 75.5 | 24.5 | 20.8 | 50.0 | 50.0 |
| 4 | Food waste - Run 4 | 78.1 | 21.9 | 18.2 | 40.0 | 60.0 |
| 5 | Vegetable market waste - Run 5 | 69.4 | 30.6 | 24.2 | 30.0 | 45.0 |

TABLE 2

Performance of biomethanation plant at different operating conditions

| | | Primary digester | | Main digester | | | | | Biogas composition (vol %) | |
|---|---|---|---|---|---|---|---|---|---|---|
| | Feed stock | Organic loading rate (kg VS m$^{-3}$ d$^{-1}$) of feed to primary digester | HRT in primary digester(d) | VS reduction (%) | HRT in main digester(d) | Liquid fraction COD (mg/L) at main digester inlet | COD removal (%) | Biogas yield (Nm$^3$/kg VS) | Methane yield (Nm$^3$/kg VS) | CH$_4$ | CO$_2$ |
| 1 | Food waste - Run 1 | 12.9 | 6 | 86.2 | 2.1 | 46784 | 95.4 | 0.527 | 0.440 | 83.4 | 15.5 |
| 2 | Vegetable market waste - Run 2 | 12.7 | 6 | 80.5 | 2.1 | 55234 | 93.3 | 0.422 | 0.342 | 81.1 | 17.2 |
| 3 | Food waste - Run 3 | 13.9 | 7.5 | 85.1 | 2.7 | 63515 | 96.1 | 0.507 | 0.433 | 85.5 | 13.4 |
| 4 | Food waste - Run 4 | 11.1 | 7.5 | 88.4 | 2.5 | 49555 | 97.2 | 0.516 | 0.438 | 84.9 | 14 |
| 5 | Vegetable market waste - Run 5 | 9.68 | 7.5 | 83.2 | 2.7 | 57805 | 96.3 | 0.425 | 0.35 | 82.3 | 15.9 |

It was observed that the biomethanation plant with food waste as feedstock released higher biogas yield with methane content in the range 84.9-85.5.

While specific language has been used to describe the present subject matter, any limitations arising on account thereto, are not intended. As would be apparent to a person in the art, various working modifications may be made to the method in order to implement the inventive concept as taught herein.

Technical Advantages of the Invention:

The present invention has the following advantage over the prior arts:

Generates biogas with high methane content (80-86%) and

Improved organic conversion efficiency in both primary and main digesters.

Generated biogas requires relatively less downstream biogas upgradation to convert it bio-CNG meeting automotive CNG requirements.

The invention claimed is:

1. A device for converting organic waste to biogas, the device comprising:
   a shredder adapted to shred organic waste to generate shredded organic waste, wherein the shredded organic waste has a reduced particle size;
   a feed preparation tank adapted to hold the shredded organic waste and water to prepare a homogenized organic waste slurry;
   a first slurry pump adapted to transfer the homogenized organic waste slurry from the feed preparation tank to a primary digester, wherein the primary digester is adapted to convert biodegradable organic fractions in the homogenized organic waste slurry to biogas and digested waste slurry, wherein the digested waste slurry comprises water soluble volatile fatty acids and alcohols;
   a neutralization tank adapted to change pH of the digested organic waste slurry by adding alkali solution to obtain neutralized primary digested slurry;
   a second slurry pump adapted to feed the neutralized primary digested slurry to a solid liquid separator, wherein the
   the solid liquid separator is adapted to separate the neutralized primary digested slurry to a residual solid sludge and a liquid leachate;
   a feed holding tank adapted to hold the liquid leachate comprising volatile fatty acids and alcohols;
   a feed pump to feed the liquid leachate to a main digester, wherein the main digester is adapted to convert the liquid leachate to biogas by methanogenic microbial culture;
   a tube settler adapted to separate the residual solid sludge from an overflow effluent of the main digester; and
   a biogas balloon adapted to store generated biogas.

2. The device as claimed in claim 1, wherein the primary digester has hydrolytic and acidogenic microorganisms to convert the organic waste slurry to biogas and digested organic slurry.

3. The device as claimed in claim 1, wherein the pH change in the neutralization tank is in a range of 6.8-7.5.

4. The device as claimed in claim 1, wherein the pH is adjusted by alkali solutions, wherein the alkali solutions comprise slaked lime, sodium hydroxide and sodium carbonate.

5. The device as claimed in claim 1, wherein the homogenized organic waste slurry is fed to the primary digester intermittently or continuously.

6. The device as claimed in claim 1, wherein the shredded particle size is in a range of 2-15 mm.

7. The device as claimed in claim 1, wherein the liquid leachate is fed to the main digester intermittently or continuously.

8. The device as claimed in claim 1, wherein the solid liquid separator is a screw filter press or a centrifuge.

9. The device as claimed in claim 1, wherein the primary digester and the main digester are in a volumetric ratio of 1.5-3.0.

10. The device as claimed in claim 1, wherein the main digester has a ratio of length to diameter in a range of 1-1.8.

11. The device as claimed in claim 1, wherein the primary digester comprises a plurality of internal baffle plates adapted to guide a flow direction of the organic waste slurry, and to avoid a short circuit and back mixing of contents of the primary digester.

12. The device as claimed in claim 11, wherein the plurality of the internal baffles divides the primary digester into three chambers, wherein each chamber comprises:
- a horizontal or a vertical agitator for mixing the contents of the primary digester;
- a temperature sensor;
- a heater;
- a temperature controller;
- a thermal insulation to avoid heat loss and to maintain a temperature in a range of 35-45 deg C; and
- a drain valve in each chamber adapted to separate non-biodegradable fractions settled at a bottom of the primary digester.

13. The device as claimed in claim 12, wherein the organic waste slurry in each chamber has a residence time of 36-60 hours.

14. The device as claimed in claim 1, wherein the main digester comprises a plurality of internal baffle plates adapted to guide a flow direction of the liquid leachate, and to avoid a short circuit and back mixing of contents of the main digester.

15. The device as claimed in claim 14, wherein the plurality of internal baffles divide the main digester into a minimum of two chambers, each chamber comprises:
- a temperature sensor;
- a heater;
- a temperature controller; and
- a thermal insulation to avoid heat loss and to maintain temperature in a range of 35-45 deg C; and
- a drain valve in each chamber adapted to drain out settled non-biodegradable fractions from digester bottom.

16. The main digester as claimed in claim 15, wherein the neutralized leachate in each chamber has a residence time of 24-48 hours depending on COD of the leachate.

* * * * *